United States Patent [19]

Natelson

[11] 4,264,560

[45] Apr. 28, 1981

[54] CLINICAL ANALYTICAL SYSTEM

[76] Inventor: Samuel Natelson, 925 Southgate Rd., Knoxville, Tenn. 37914

[21] Appl. No.: 106,550

[22] Filed: Dec. 26, 1979

[51] Int. Cl.³ .................... G01N 35/04; G01N 35/06; G01N 31/22; G01N 21/05

[52] U.S. Cl. .................................. 422/58; 356/246; 422/57; 422/61; 422/66; 422/81

[58] Field of Search ...................... 422/56, 57, 58, 61, 422/66, 81, 82; 23/901; 356/246

[56] References Cited

U.S. PATENT DOCUMENTS

| | | | |
|---|---|---|---|
| 3,723,064 | 3/1973 | Liotta | 422/57 X |
| 3,917,453 | 11/1975 | Milligan et al. | 422/56 X |
| 3,918,910 | 11/1975 | Soya et al. | 422/56 |
| 4,108,729 | 8/1978 | Mennan | 422/57 X |
| 4,110,079 | 8/1978 | Schaeffer et al. | 422/56 |
| 4,178,153 | 12/1979 | Sodickson | 422/56 X |

Primary Examiner—Ronald Serwin
Attorney, Agent, or Firm—George B. Oujevolk

[57] ABSTRACT

An arrangement for chemical analysis of a small quantity of sample wherein a specimen of a small size is passed through a porous distribution first medium onto a reagent-containing second medium is disclosed. The reagent-containing second medium is a thin, flat, liquid-impervious medium. A reagent is encapsulated upon the second medium as a flat, liquid-phase surface. The first and second mediums are so arranged and disposed that when firmly pressed together, the encapsulated liquid reagent will be liberated and the specimen will be distributed through the first medium onto the liquid-phase liberated reagent where the subsequent reaction of the liquid-phase reagent and the specimen can then be identified by reading means.

12 Claims, 22 Drawing Figures

CLINICAL ANALYTICAL SYSTEM

The present invention relates to a system for clinical chemical analysis, more particularly to a system which can be used by inexperienced personnel. The system may be automated.

BRIEF REVIEW OF THE PRIOR ART

In the laboratory of clinical chemistry, two major arrangements are in general use. One arrangement is directed to the analysis of single components in biological fluids. This arrangement is used in smaller medical institutions and as an emergency system in larger hospitals. Two such instruments commonly used are the ACA-analyzer of the DuPont Corporation, and the Stat-Pack unit of Technicon. In these instruments, a package is provided, serum is added, the package is placed in a machine and the machine processes automatically the addition of the reagents contained in the package and the readout of the results. The advantage of this arrangement is that the operator can select a package for a particular test at any time of the day or night without personally having the necessary skill to do these tests.

A second arrangement is the multi-analyzer arrangement. This arrangement takes a serum sample and divides it into as many as 20 aliquots, analyzes each aliquot separately and reports the result, with the aid of a computer, on a single chart for a particular patient. Examples of this arrangement are the SMAC instrument of Technicon and the Hi-Cell instrument. This second arrangement is usually used for the daily workload and for the screening of the blood of new patients.

These two arrangements hereinbefore described perform the bulk of the tests done daily in both commercial and hospital laboratories of clinical chemistry. It is necessary however to provide a single system capable of performing the functions of both of the arrangements hereinbefore described on a much smaller sample, more rapidly and at a substantially lower cost.

BACKGROUND OF THE INVENTION

On Mar. 14, 1960 Dr. Samuel Natelson, the inventor herein filed U.S. patent application Ser. No. 14,894, entitled "Automatic Chemical Analyzer". This application issued as U.S. Pat. No. 3,036,893 on May 29, 1962. This patent describes an arrangement for chemical analysis using three tapes or layers, both terms being synonymous terms. The sample was placed on a sample receiving tape to hold and evenly spread the sample. This sample receiving tape or layer was in contact with an intermediate porous tape designed to filter off unwanted components and to produce an even stain on a third test tape. The reason for the intermediate porous tape is described at length in the aforesaid U.S. Pat. No. 3,036,893. This patent established certain principles for the success of a layered tape system of chemical analysis.

1. The sample had to be spread evenly on the sample receiving tape. Since diffusion is too slow, capillarity had to be used to cause rapid spreading. This was done by paper or cloth. It was also established that the spread needed to be controlled since the same volume of serum and water did not spread to the same area. Confinement of the spread was recommended and explained in the aforesaid patent.
2. The porous tape could use pores which can be seen under a microscope, as in bacterial filters with parchment, or submicroscopic pores as in cellophane.
3. The sample receiving tape and test tape could be backed with plastic so as to provide support.
4. The tapes or layers could be assembled in a continuous system, in the form of continuous tapes for the sequential analysis of different specimens.
5. The system was flexible since numerous tests could be performed with the system such as glucose, amino acid nitrogen, calcium, magnesium, protein, total lipids, and radioactive inorganic iodine. Under proper conditions, this type of test can be adapted for radio-immunoassay.
6. The system also taught the separation of tapes and the reading of the colored spots on the test tape by means of a densitometer or spectrophotometer, or, where radioactivity was present, by a gamma counter or scintillation counter.
7. Methods were described for carrying out reactions at elevated temperatures and for automatically adding a sample.

A continuation application of U.S. Pat. No. 3,036,893 introduced for the first time the concept of simultaneous analysis of specimens on a layered system containing a sample receiving tape, a porous tape, and a reagent tape. This continuation application issued as U.S. Pat. No. 3,216,804. In this system, a reagent was added to a large circle of filter paper. This was covered with a circle of cellophane, as the porous tape, and finally a circle of filter paper (liquid receiving tape) was placed on top to receive the specimen. The samples or specimens were added simultaneously from capillary tubes containing the samples to be analyzed. In addition this patent contained a description for the preparation of "non-grainy paper", for the even spreading of the specimen. The tapes were in the form of large filter papers and the samples were disposed in a circle near the outer perimeter. U.S. Pat. Nos. 3,216,804 and 3,036,893 demonstrated completely automated systems.

The advances made in U.S. Pat. No. 3,216,804 were as follows:

8. The use of non-grainy paper in the "test" tape for even spreading.
9. The simultaneous administration of specimens to a multi-layered test system for analysis.

A divisional application of U.S. Pat. No. 3,036,893 issued as U.S. Pat. No. 3,261,668. This patent covered three flatstrip mediums, one being absorbant and designed to receive a sample, the second being porous to water and proteins but impervious to substances with a molecular weight higher than proteins, e.g., erythrocytes, and finally a test medium which was the third tape. The patent also provided for an impervious backing to the tapes, for confined spots, and for reagents to be contained in the test tape for analysis. Thus, U.S. Pat. No. 3,261,668 provided for the general tape system regardless of the composition of the tapes, provided that they had the property of absorbancy and porosity as required by the basic patent. The porosity of the intermediate tape could vary, but was such as to permit the passage of molecules of a size up to and including proteins, but not larger particles such as cells. This patent also introduced the concept of individual samples being set up for a particular test so that the operator could add the specimen to the receiving layer which was an integral part of a pad. This pad had upper and lower plastic covers and three tapes all encased in a plastic cover. The operator removed the cover and placed the sample on the sample receiving tape. The pad was closed and placed in a press plate for a fixed period of time. The sample passed to the test tape through the porous tape. The stain formed on the test tape was then read. The operator could keep a stock of different pads, one for each test, ready at any time for rapid analysis. This pad arrangement performs simple, but diverse tests required for the usual tests required by a small hospital laboratory or a physician's laboratory. While U.S. Pat. No. 3,261,688 recommended turning the upper tape down, so that the side to which the sample was applied faced the porous tape, it also shows that this was not essential and the desired component in the sample would pass through to the reagent tape and that many tests could be performed without moving the upper tape. This system also permitted the analysis of several samples or standards simultaneously.

Subsequently, several other U.S. patents were granted in the name of Samuel Natelson relating to automated chemical analysis systems, for laboratory and physician's use. These include U.S. Pat. Nos. 3,260,413; 3,368,872; 3,502,438; 3,219,416, and 3,502,438.

In U.S. Pat. No. 3,502,438, the inventor describes a system for moving and separating a multi-tape system for analysis. This system shows the method of reading the spot produced on the test tape by fluorescence or transmission. The patent also shows a method of reading a blank area by transmission, to be subtracted from the reading of the absorbance of the spot where the color has developed. Thus, it shows the analysis by means of a dual light beam system.

In U.S. Pat. No. 3,368,872 an instrument is described for moving the porous and test tape, bonded together, the test tape containing an impregnated reagent. Means are provided for emptying capillary tubes on a moving porous tape so that the component to be analyzed will diffuse through to the test tape for analysis. This system is intended for sequential analysis. In U.S. Pat. No. 3,915,652 the present inventor describes an improved method for adding specimens from capillary tubes on to a tape arrangement for analysis. This arrangement is especially useful in implementing one of the objects of the present invention.

Another apparatus which is useful in connection with the present inventive concept is described in the Samuel Natelson U.S. Pat. No. 4,004,150. This patent describes the use of a scanning wheel in evaluating the light intensity emitted from spots either by transmission, reflection or fluorescence. The spots in an array can be scanned electronically as with a television camera, the signals being discriminated and evaluated by a computer.

Some of the foregoing techniques as well as other inovations are described by Samuel Natelson in *MICROCHEMICAL JOURNAL,* Volume 13, Number 3, September 1968, pages 433–458 entitled: AUTOMATIC ANALYSIS OF MICROSAMPLES CONTAINED IN CAPILLARIES WITH A MICROSAMPLE DISPENSER.

Other technicians entering the field have also obtained patents, e.g., U.S. Pat. No. 3,992,158. In this patent, the flat strip medium designed to receive a sample is called the "spreading layer". Just as the sample receiving tape of Samuel Natelson spreads the sample by capillarity, a similar result is obtained by using various powders such as diatomaceous earth, titanium dioxide or glass beads to obtain capillarity for the rapid spreading required. The porous strip medium, intermediate the other two layers designed to filter out unwanted components is described in this patent as the filtering layer. The flat strip medium designed to carry the reagent, is called the reagent layer. The supports for the system correspond to those described in the aforementioned Samuel Natelson U.S. patents. A reflecting layer is provided. This feature is inherent in the construction described in the aforementioned Samuel Natelson patents since the filter paper is a reflecting medium which is also translucent. The porous tape described by Samuel Natelson in his patents, which has pores of a size which will not allow protein to pass through, as in the Samuel Natelson U.S. Pat. No. 3,261,668 is called a dialysis layer in U.S. Pat. No. 3,992,158.

However, none of the aforementioned U.S. patents describe a system where reactions carried out in a test tube in the laboratory can be used directly, without substantially modifying the composition of the reagents. Furthermore, certain tests which do not produce a change in absorbance, fluorescence or reflectance, such as with ion specific electrodes cannot be applied directly to the systems described in the aforementioned U.S. patents.

SUMMARY OF THE INVENTION

Generally speaking, according to the present invention, improvements are made in the basic concept for use of a multilayered system in the analysis of fluids for various components. The major improvement is in the construction of the "flat strip medium" which is the test medium. The object is to take advantage of the conventional wet chemical procedures, which have been developed thoroughly by analytical chemists, and apply them with as little change as possible. The various test kits, sold for enzymatic analysis or for radioimmunoassay can be applied readily to this proposed novel system. The system contemplated can perform tests using ion specific electrodes for readouts. It puts no significant restraints on the ingenuity of the chemists. If it is workable in a test tube on earth, it will work in this system in space. The system can be used as pads for individual tests at any time of the day or night or can be used in a system for the simultaneous sequential analysis of a plurality of specimens. This system can also be used for the analysis of a plurality of components simultaneously, in a single specimen. Sample size is in the microliter range and results can be available as fast as 400 per hour after the first specimen has been processed, in sequential analysis. In addition, it is practicable with this system, to sample the specimen from the fingertip at a collecting center, carry the pad to a processing area and process the specimen several hours after collecting the specimen, provided that the component in the specimen is stable in a refrigerator or freezer. A further advantage of this system is the ease of construction of the apparatus required for readout and printout of the results, with built-in identity correlating the results with the specimen of the patient being tested. The system uses a small amount of sample such as can be obtained by fingertip puncture and can be used in a pediatric laboratory where present multi-test automated systems have been found to be impractical. The present invention replaces the reagent layer (also referred to in various patents as the test tape, reagent tape, reagent layer and film medium for applying reagent) with a structure designed to hold the reagent in the liquid state, in the form of a thin film or layer, and, at a propitious time, to permit the reagent to react with the component of the fluid being analyzed. The thin film then develops changes in its properties which can be monitored by reflectance, absorbance, fluorescence, radioactive emission, or by an electrode such as for $pCO_2$, $pO_2$ or for specific ion determination.

The invention as well as other objects and advantages thereof will become more readily apparent from the following detailed description, when taken together with the accompanying drawing, in which:

BRIEF DESCRIPTION OF THE DRAWINGS

FIG. 1b presents in perspective a top view of an arrangement for sample collection by the system of FIG. 1a;

FIG. 2c again is a cross-sectional illustration of still another arrangement similar to FIG. 2a;

FIG. 2d shows a portion of the arrangement of FIG. 2c in a top perspective view;

FIG. 2e is an explanation of the encasing of a liquid reagent using a spacer in a cross-sectional view;

FIG. 2f shows a top view of a portion of the spacer arrangement of FIG. 1e;

FIG. 2g depicts a system, in cross-section of applying a reagent to its medium using a syringe;

FIG. 2h represents a perspective view of the reagent medium used in connection with the arrangement of FIG. 2g;

FIG. 7 explains optical integration of a sample in perspective;

DETAILED DESCRIPTION

Broadly stated, the present invention makes use of the multi-layered flat medium arrangement heretofore described by the present inventor in the aforementioned prior art patents of this same inventor, but using a reagent in the liquid phase.

Figure 1A:
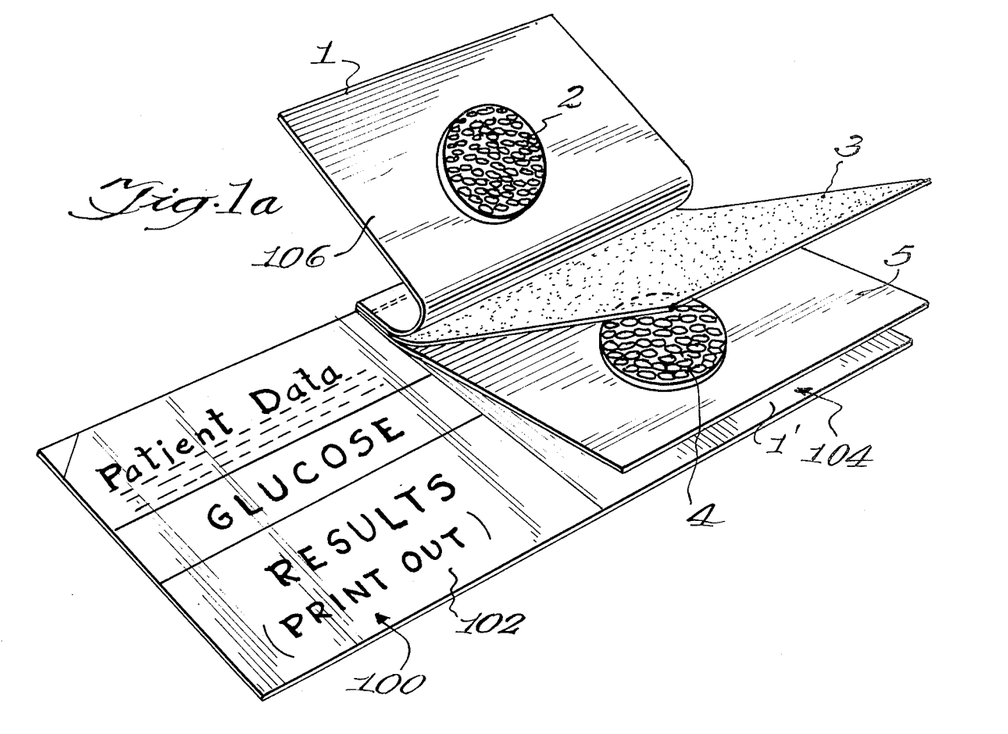
FIG. 1a is a perspective view of a layered pad contemplated herein attached to a computer card.

In the drawings, FIG. 1a shows a data processing card 100 where the patient data is shown on the left side 102 and the right side 104 has the one-use test pad 106 contemplated herein.

The one-use test pad 106 on the right hand side of the data processing card 104 has several mediums or layers and consists of upper and lower covers, 1 and 5 which may be of the same material as herein described; there is a sample receiving medium 2, also called a sample distributor, and since it often contains a confined spot, is sometimes referred to as the confined spot. This confined spot can also be firmly affixed to the upper cover 1. Next, there is a porous or intermediate layer 3, and finally the liquid phase reagent medium 4.

The data processing card 100 has on the left hand side 102 the necessary information about the patient, and in addition to the regular patient data, the type of test processed on the one-use test pad 106.

As will be described herein in greater detail, the reagent medium 4 contains the reagent in the liquid phase, i.e., the reagent is encapsulated as the reagent medium. The one-use pad 106 which is attached to the computer card is processed in a pressure-applying zone. This releases the reagent. Readout means are provided to read the change in optical properties of the liquid film by reflectance through a transparent portion of the data processing card or through a hole in the bottom of the card. The readout results are printed on the card. The one-test pad 106 is removed and the card is the patient's report.

Figure 1B:
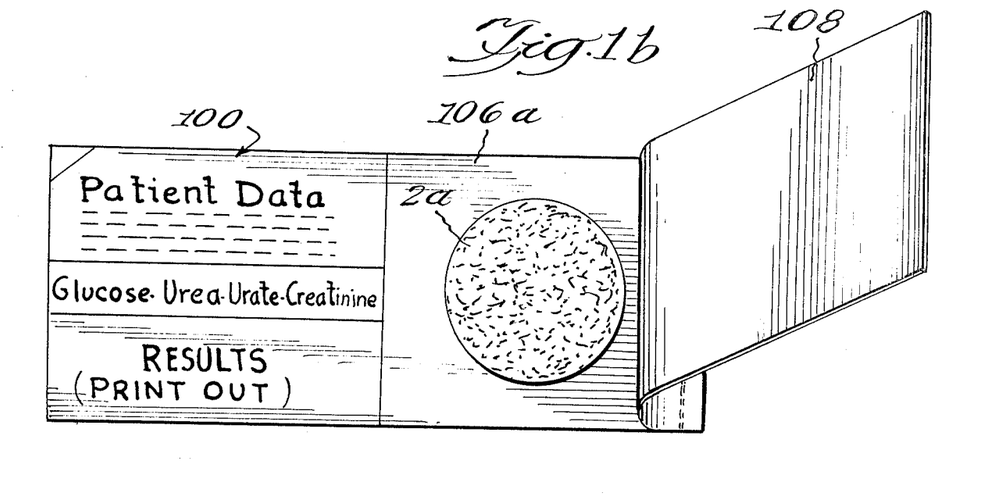

In FIG. 1b, the same computer card is used as in FIG. 1a. The pad 106a however has a sample receiving medium or sample distributor 2a in the form of a filter paper or powdered cellulose of 1¼ inch in diameter. As the specimen needs to be transported to the laboratory, a dust cover 108 can advantageously be used.

Figure 2A:
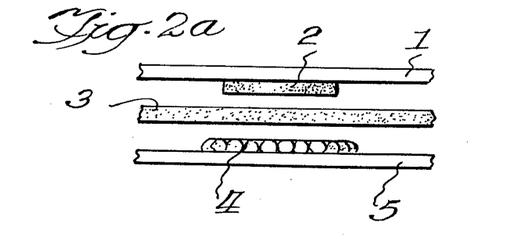
FIG. 2a is a cross-sectional view of a three-layer pad contemplated herein showing the various mediums, and their use according to the inventive concept.

The arrangement shown in FIG. 1a is shown in cross-section in FIG. 2a which depicts the sample receiving film medium 2 that is supplied for receiving a specimen. This film medium 2 is about 1 to 3 mils in thickness. A specimen is applied to this medium either manually or from an automated sampling device. The receiving film medium 2 is in the form of a disc located on the plastic cover 1. This disc has variously been termed a confined spot or sample distributor, and can be made of filter paper, non-grainy filter paper, cloth, powdered cellulose or of materials used in thin layer chromatography, such as aluminum oxide, gypsum and silica, finely powdered and supported on a plastic, metal or glass base. The plastic support, 1, for the sample distributor or sample receiving film medium also serves as the cover.

The intermediate filter medium 3 is porous to the component being analyzed but not to interfering substances. It is made of cellophane, cellulose acetate or other non-reactive plastic of a selected porosity, so that molecules up to and including the size of proteins can pass, but not cells. This intermediate film medium 3 has a dual purpose. It filters off unwanted components and also serves as a cover for the thin fluid film of reagent 4. It distributes the perfusate into the fluid liquid layer evenly. For this reason, it needs to be of a strength that does not rupture readily when wet. Cellophane or cellulose acetate 0.5 mil in thickness can serve this purpose. Certain non-porous films such as Mylar or Nylon can also be used, if first rendered porous by puncturing with an electron beam. In the case of gas analysis, such as CO, $CO_2$, or oxygen, thin sheets of Teflon, polypropylene or silicone rubber are practicable since they are pervious to the gas. All of the structures shown in FIGS. 2a through 2n made use of the sample receiving film medium 2 for receiving the specimen and the intermediate porous film medium 3. According to the present inventive concept, the reagent medium, described in the Samuel Natelson prior art patents hereinbefore mentioned is replaced by a liquid phase reagent which is formed in any one of several ways. In one form it is encapsulated on the lower cover or bottom layer 5 in the liquid phase.

Figure 2B:
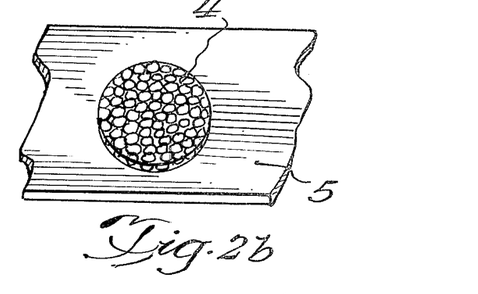
FIG. 2b presents a top perspective view of a portion of the pad shown in FIG. 2a with emphasis on the encased reagent.

The encapsulated liquid phase reagent film medium better seen in FIG. 2b is disposed so as to contact the underside of the porous medium 3. The underside of the reagent-containing medium is backed by a transparent plastic film 5 which is impervious to water. The encapsulated film medium 4 is prepared in one of several ways. In one procedure, a thin film of reagent is sprayed on a transparent film of plastic. A solution of plastic such as styrene is then sprayed over the liquid phase reagent. This provides a continuous film of encapsulated reagent 4 encased in a brittle casing whose thickness does not exceed 0.2 mm. This can be formed in a continuous tape. Using a tool such as a cork borer, discs, containing the reagent, of approximately 2 cm diameter as an example, are cut out. A disc is mounted on the plastic support, sealing the edges, and gluing to the plastic support at the same time. If more than one reagent is added in a particular test, a second disc 4' is encapsulated and placed above the first as shown in FIG. 2i and FIG. 2j.

A preferred way of encapsulating the reagent is to use a mold having a part consisting of hemispheric mounds and corresponding female parts with depressions on the surface of a flat piece of steel. The mold serves to emboss a strip of plastic such as polystyrene film with a circular design about 2 cm in diameter. Within the circle are embossed hemispheric depressions about 1 mm in diameter. Thus, about 10 hemispheres will transverse the diameter of the overall circular design, each 1 mm in diameter. Since the area of a circle is $3.14154 \times r^2$, it is apparent that there will be about 75 depressions in each circle. If the depressions are filled with reagent, and matched with a second such film, and the two sealed together, the structure will be similar to that obtained by spraying only the capsules will be larger. When formed by spray, the encapsulation is referred to as micro-encapsulation. By the method of the present description, it is referred to as milli-encapsulation.

Another variation of the structure shown in FIG. 2a and FIG. 2b is to apply pressure with a mold, and while the film rests in the female section of the die, to remove the male portion and to add reagent and sweep off the excess. If this is now covered with the plastic support and pressure is applied, the plastic support seals the embossed film and the reagent is encapsulated in the form of hemispheres. This can be lifted up and the process repeated, using a feed of 1 mil polystyrene for the film to be embossed and a film of 1 mm of styrene as an example for the supporting film. This results in an endless tape with circles of encapsulated reagent at a distance of about 2 cm apart. This can be cut or used as a tape for the automated systems as will be described later herein. It is to be observed that the film of reagent is now in a confined area.

A second disc 6 of inert porous material such as nongrainy paper, slightly smaller than the disc of encapsulated reagent 5, can be interposed between the porous medium 3 and the encapsulated reagent 5. This serves to distribute the reagent when released. The reagent will then be directed to a confined area as shown in FIG. 2c and 2d.

The volume of reagent which is used in the encapsulated layer in the illustrations given does not exceed the volume of a cylinder 0.5 to 2 cm diameter and 0.1 to 1 mm high. This is in the general range of 20 to 300 microliters. A flat circular cylinder or square shaped groove of this capacity can thus serve as the liquid film medium. This principle is shown in FIG. 2e. A tape 9 of plastic impervious to water, such as polystyrene, polyethyethylene or Mylar is placed on the supporting medium 1'. A cylindrical opening 7 in the tape as shown in FIG. 1f is cut out. In addition, slots are cut 7' to communicate with the central cylinder. These channels are 0.1 mm wide. This structure serves as a spacer and is 1 to 3 mils in thickness, as an example. The cylindrical container 7 communicates with a deflated overflow plastic container 10. The cylindrical container 7 thus defined in the center is bounded on top by the porous tape 3 and on the bottom by the plastic support 1' which forms its upper and lower surfaces, respectively. The channels 7' serve for feeding liquid reagent into and out of the cylinder. In FIG. 2e a pear-shaped flexible container 8 with reagent communicates with the entrance to the cylinder by means of a readily ruptured diaphragm, and is sealed to and made part of the structure. Alternatively, a syringe, fitted with a fine needle, can be inserted into the entrance channel 7'. The exit channel 7" communicates with the deflated plastic container 10 which can expand when liquid is forced into it by way of the exit channel. Thus, container 10 is the overflow plastic container.

Figures 2C, 2E, 2F, 2G, 2H:
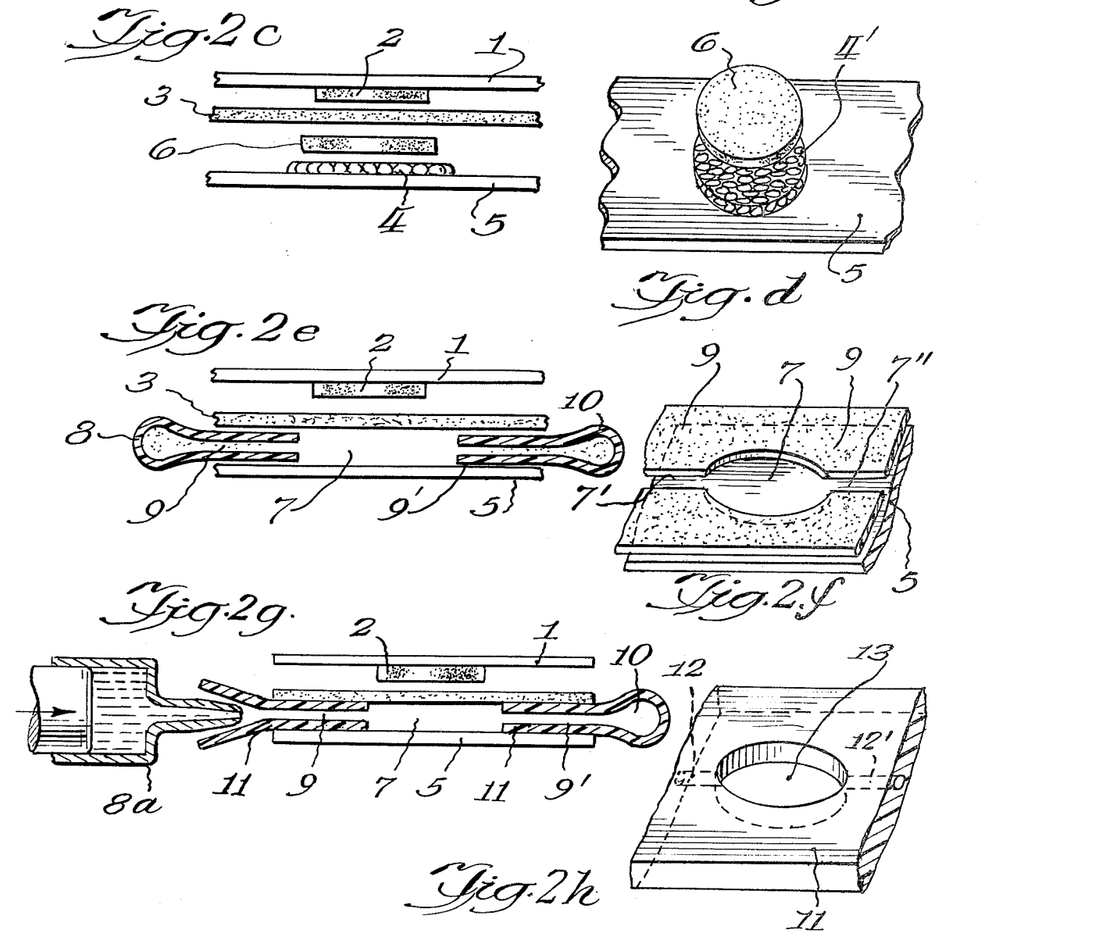
Figures 2I, 2J, 2K, 2L, 2M:
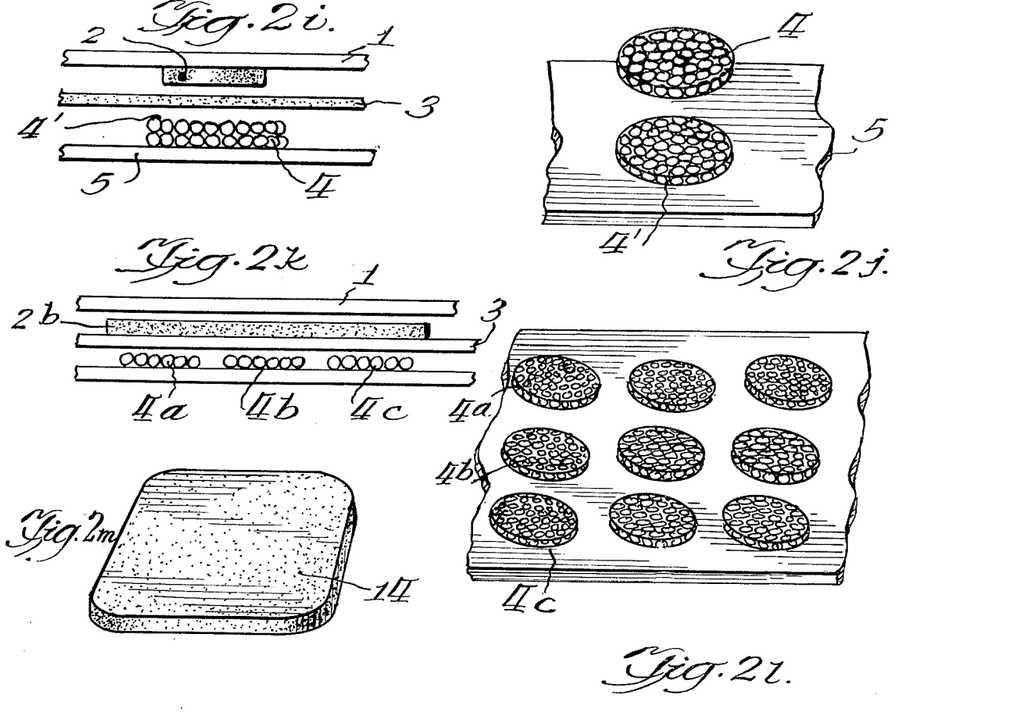
FIG. 2i has the encapsulated reagents disposed separately and shows in cross-section how different separate encapsulated reagents can be placed in connection with the reagent medium.
FIG. 2j is a top perspective view of FIG. 2i.
FIG. 2k illustrates in cross-section an arrangement where the reagent layer has a plurality of reagent locations so that different tests can be performed with only one pad.
FIG. 2l provides a perspective view of a portion of the arrangement shown in FIG. 2k.
FIG. 2m provides a three dimensional view of a portion of FIG. 2k.

A variation of the structure shown in FIG. 2e is to make the spacer from rigid plastic by drilling a hole about 0.5 to 2 cm wide in the plastic, and then drilling capillaries in the side 12 and 12' to communicate with the central hole. If acrylamide plastic is used for this purpose, as an example, stiff "piano wire" can be heated and forced into the plastic to form fine capillaries. These channels are about 0.1 mm bore in a plastic spacer 11 of about 0.5 to 1 mm in thickness as illustrated in FIG. 2f. The structure in FIG. 2g shows a cross-sectional view with a syringe 8a communicating through the entrance channel to a central cylinder 7 and the overflow container 10 communicating with the central cylinder 7 from the opposite side. If plastic spacer 11 is 1 mm in thickness, it is advantageous to fill the cylinder with glass beads (washed, 400 mesh) to decrease the void volume so as to use less reagent, and thus dilute the color developed less, to increase sensitivity. The cylindric reagent container 7 may alternatively be covered with a slightly larger disc of absorbant material as indicated in FIGS. 2c and 2d. In this case, it has to be slightly larger to be supported on the walls of the cylinder.

Figure 2N:
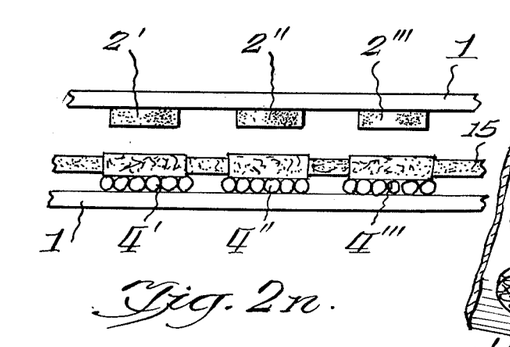
FIG. 2n provides another embodiment of the concept of the invention depicted in FIG. 2k.
Figure 2O:
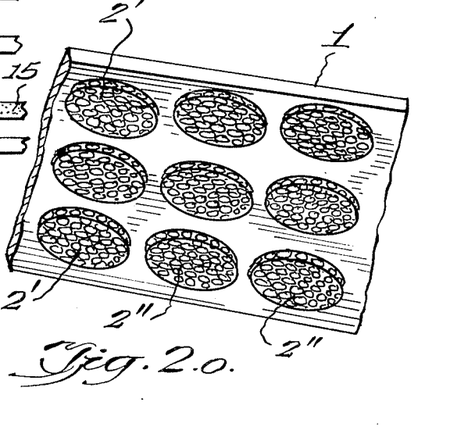
FIG. 2o is a perspective view from underneath the sample receiving medium or sample distributor wherein a plurality of samples are to be processed.

A series of different reagent disce 4,4' as shown in FIG. 2i can be stacked vertically so as to mix and function in this multilayer system, and this is shown in a three-dimensional view in FIG. 2j illustrating the stacked arrangement of FIG. 2i with reagents 4, 4'. The reagents for different tests can also be disposed in rows, and FIG. 2k shows a plurality of different reagent discs, 4a,4b,4c in the liquid phase, disposed in rows for the analysis of different components in the same specimen. FIG. 2l and 2m are three-dimensional views of a portion of this system showing the sample distributor and rows of reagents 4a,4b,4c. FIG. 2n shows a view having rows of porous intermediate discs 3',3",3'" used for the assay of the same or different components in the same specimen 2', 2", 2'" simultaneously. FIG. 2o presents in three dimensions a view of the sample receiving medium separated from the structure shown in FIG. 2n by the intermediate porous medium showing rows of specimens 2, 2', 2'".

Figure 3:
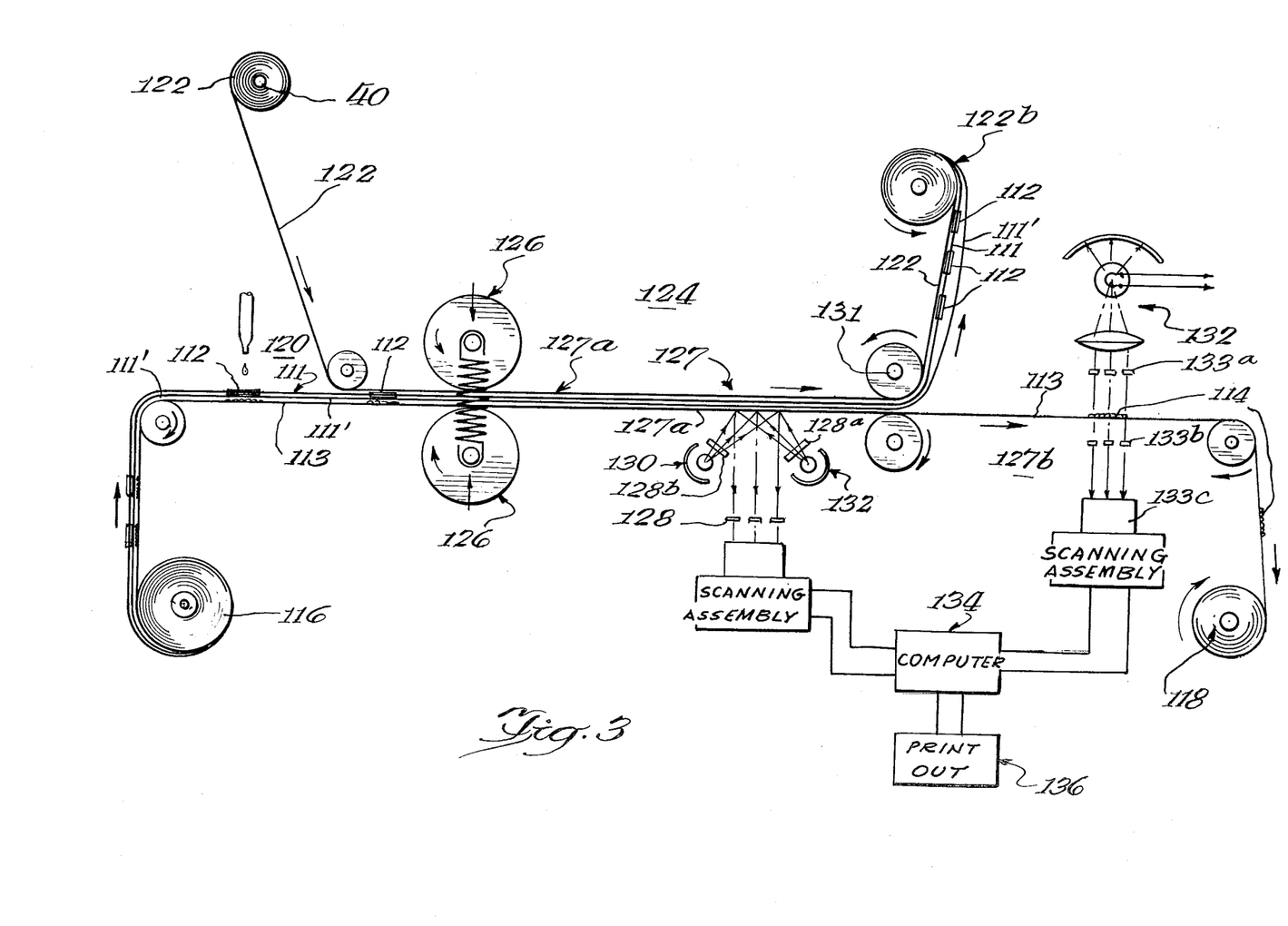
FIG. 3 is a sectional side view of an automated arrangement for the embodiments shown in FIG. 2k and FIG. 2l.

The system described may also be automated as depicted in FIG. 3, showing an elongated sample receiving tape medium 111 carrying sample distributors, e.g., confined spots 112, an intermediate porous medium 111' disposed to move with the elongated sample receiving medium 111, a second elongated medium 113 carrying capsules 114 of encapsulated reagent thereof (not shown). The mechanical support for this type of instrument has likewise heretofore been described by Samuel Natelson in the aforementioned prior art patents. At the input end there is a pay-off reel 116 and at the output end there is a take-up reel 118.

Other pay-off reels and take-up reels are likewise provided for the other tapes where needed. The three mediums, i.e., the sample receiving medium 111, intermediate porous medium 113 and encapsulated reagent medium 111' pass a sample dispensing work station 120 where a sample is placed on one of the sample distributors, e.g., confined spot 112. A cover tape 122 is dispensed from another pay-off reel 122a to cover the other mediums. The four tapes then enter a reaction zone 124 first passing through spring loaded rollers 126 to break the reagent capsules. Reaction then takes place between sample and reagent in the reaction zone. The four top tapes pass to the readout zone 127 where light means 130, 132 are applied to the medium to be read by reflection. The cover medium, receiving the porous tapes are removed by a take-up reel 122b and a drive mechanism 126. Readout of the color developed in the reagent is read out by transmission by light source 132, filters 133a and 133b and detector of scanning assembly 133c.

In the arrangement of FIG. 3, the elongated transparent film 113, (e.g., cellulose acetate or Mylar) carries the arrangement shown in FIG. 2l. An array of different reagents, contained in hemispherical containers, is disposed on the transparent elongated carrying tape. Structures such as shown in FIG. 2f can readily be substituted to provide a liquid phase reagent. In carrying the invention into practice it has been found practicable to have reagent carrying discs of 0.5 cm diameter disposed at 0.3 cm from each other. With a tape 5 cm in width, nine different reagents can readily be carried in a small space shown in FIG. 2o, either in a rectangular or circular array. The arrangement is covered with the porous tape 111' and also serves to carry the sample receiving medium 111, i.e., the sample distributor. The distributor typically is 3 mils thick and of a length and width of 3 cm. This surface will absorb and spread about 100 microliters of water. An amount of sample either diluted with buffer or undiluted is added to saturate the distributor.

The sample is covered with a plastic covering tape 122 and passes through a reaction zone 127a where reaction takes place after the capsules are crushed to release the reagent. This is done by rollers 126 which are spring loaded to apply pressure. This can also be done by flat press plates. The sample is delayed in the reaction zone to give the reagents time to initiate the reaction and then the assembly moves to the first readout zone 127 which reads by reflection and then to a second readout zone 127b which reads by transmission. The whole tape is moved by spring loaded rollers 131 which are geared to each other as described in the earlier Natelson patents.

The readout zone 127 has light filters 128 disposed under the assembly of tapes, sources of light which include an ultra-violet light 130 and a tungsten light source 132, roller drive mechanism 131 to drive the tapes through the readout zone 126. Both light sources are collimated and are moulded with filters 128a and 128b. Here the fluorescence or change in reflectance is read repetitively by the scanning device which reads the light intensity of each spot formed and then continues to read them. When the reading has reached its maximum, the result is interpreted in terms of concentration by a computer 134 and printed by a print-out 136. Alternatively, the readings are fitted into a regression line by the computer and the concentration is interpreted from the slope of the line. The monochromatic light filters 128 are provided for each reagent disc so that a different wave length can be read for each of the different specimens, if necessary.

Light from the sources 130 and 132 are provided by the ultra-violet lamp for the shorter wavelengths and by a tungsten-halogen lamp for the longer wavelengths. The instrument also provides for a readout by absorbance. In this case, a collimated light source 132 is passed through the spot produced by the reagent in the crushed discs. When the discs are crushed by the press plate, all of the encapsulated reagent is released at the same instant initiating all the reactions simultaneously.

Intermittent motion proceeds so as to place the complex of tapes, with the released reagent, in the reflecting and then or fluorescent readout zone. Motion does not begin until the readout is finished. This takes usually about twenty seconds to one minute. The rollers or press plates and the system can be heated usually to 37° C. Alternatively the point where the tapes are assembled to the end of the readout zone can be housed in a 37° C. oven. This serves to speed up the reaction rates.

When the tape driving mechanism is activated again, the tapes are moved again, so that the next array has its capsule broken and moves into the reflecting portion of the readout zone. At the same time, the specimens which have been read by reflection can now move to the transmission area portion of the readout zone and can be read by transmission. The take-up reels for the distributor tape and the bottom tape assembly are both operated from the drive mechanism for the tapes, being connected thereto by spring loaded belts.

In FIG. 3, illumination of the reflecting system is shown by means of elongated ultra violet and tungsten-halogen lamps. Either one or both can be used. Isolation of the particular wavelength to be read, is by the use of interference filters such as shown in the drawing. The porous layer can be replaced by porous discs, slightly larger than the encapsulated disc. These can be disposed in rows so that different porosity can be used for different specimens, see FIG. 2n.

Figure 4:
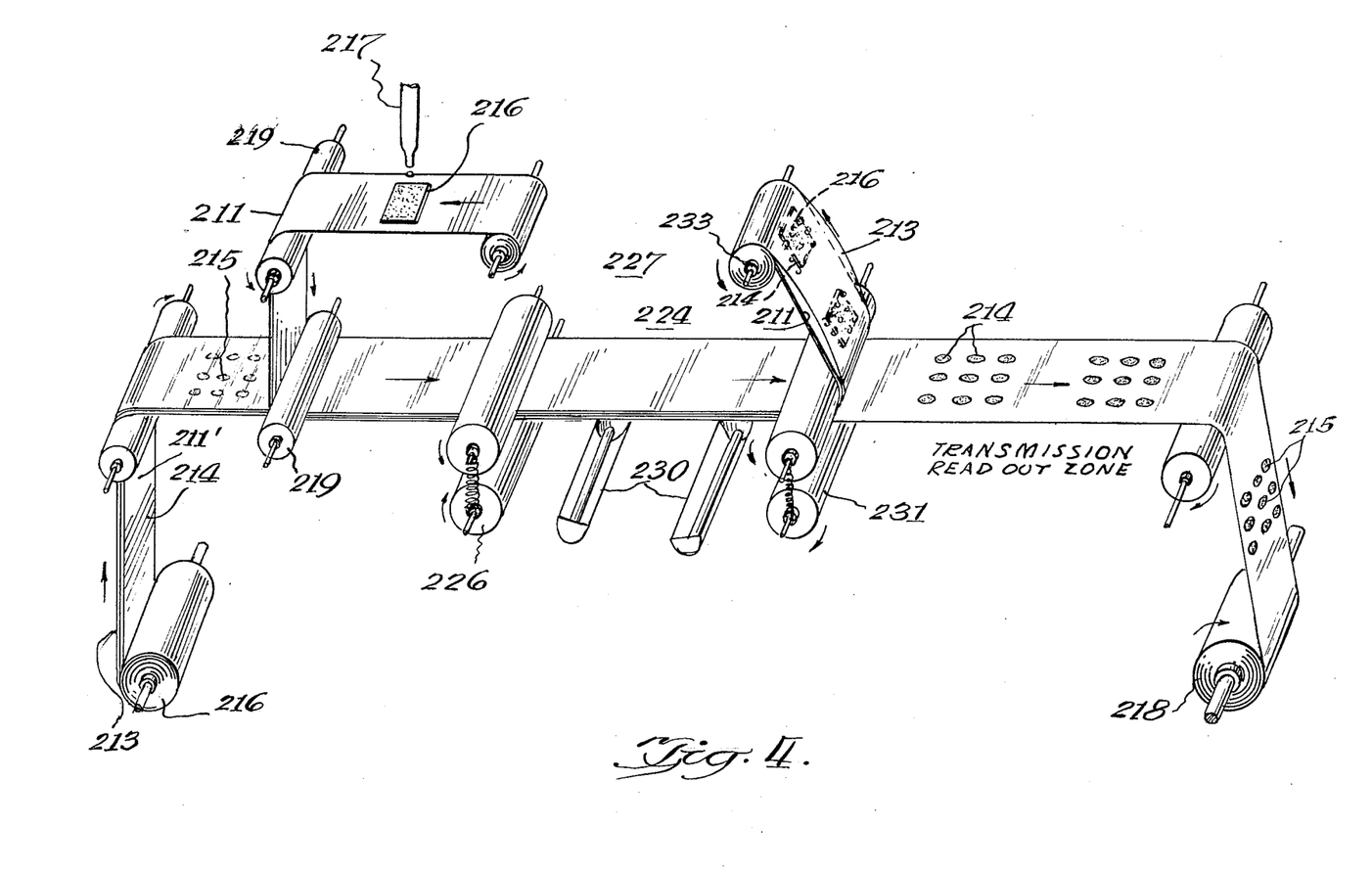
FIG. 4 is a perspective view of another version of an automated system.

A slightly different arrangement of the apparatus of FIG. 3 is shown in FIG. 4. The encapsulated reagent 214 is sealed to the bottom tape 211'. Both the bottom tape 211' and the intermediate porous tape 213 are wound on the same pay-off reel 216. The bottom tape 211' is made of plastic and this tape carries a plurality of encapsulated discs 214 arranged in rows. The intermediate porous tape 213 carries an array of porous discs 215 arranged in rows to match the position of the encapsulated discs. The sample from a capillary tube or bottle 217 is placed on the sample distributor pad 216 on the sample receiving tape 211. The direction or orientation of this tape 211 is reversed by a reversing roller 219 so that the sample on the sample distributor 216 is placed face down over the array of porous discs 215 on the intermediate tape 213. The three tapes then pass through spring-loaded rollers 226 into a readout zone 227 having a reflecting portion with reflector lamps 23o including an ultra-violet lamp and a tungsten-halogen wire lamp. It is to be observed that in this instrument, the reflection portion of the readout zone acts on the tapes when they are held together.

Between the reflection portion of the readout zone and the transmission portion, both the sample receiving tape 211 and the intermediate tape 213 with the porous discs 215 are taken up by a take-up reel 233 while the bottom tape 211' containing the encapsulated reagent continues to the transmission portion of the readout zone 230 and after reading out the results by transmission, the bottom tape 211' is finally taken up by the last take-up reel 218.

According to the arrangement in FIG. 4, the payoff reel supplies sample distributors to a sample application zone. Here, the sample 217 is added from a sample diluter or from a capillary, and the tape 211 turns over a roller to meet an assembly of porous discs on a tape and an array of reagents disposed in circles, each circle carrying the reagent in small encased hemispheres. The assembled tape system passes through a pressing zone where pressure is applied by spring loaded rollers 226 or press plates supplied for this purpose. The capsules of reagent are broken, releasing the reagents and initiating the reaction. The motion is intermittent. The tape assembly now pauses in the reflecting readout zone and the intensity of the reflected or fluorescent light is scanned through light filters, a separate one for each circle of reagent. The top tape, carrying the distributors and the porous tape are separated and the reagent carrying tape moves to an absorbance portion of the readout zone. There the transmission of light from a light source such as a halogen lamp, ultra violet lamp, and for special purposes a single or dual beam spectrometer, is measured. The transmission or reflectance or fluorescence of light is scanned using a scanning wheel of the kind described in U.S. Pat. No. 4,004,150 with light pipes as shown in FIG. 7 or by electronic means, as with a television camera. The readings, both by transmission and reflectance are interpreted by a computer, which then directs the printer 136 (shown in FIG. 3) to record the data.

For the purpose of single sample analysis, the distributor shown in FIG. 1b can be supplied in the pad in FIG. 1a. The encapsulated reagent layer can carry a plurality of circular capsules as shown in FIG. 2m. The card of FIG. 1a can then be placed in a press plate manually which is a part of the automated readout system. In this case, the bottom of the computer card has as many holes (about 3 mm) as there are encapsulated reagent circles. The reflectance or fluorescence can then be read out as the reaction proceeds. When ready, the results are printed out on the card. The operator moves the card, tears off the reaction pad and sends the card back as a report. This serves to insure the identity of the specimen and report. This whole process can readily be automated since the handling of computer cards is a well established process.

When the sample distributor is disposed on a computer card as shown in FIG. 1b, a dust cover 108 is supplied to protect the specimen being analyzed. At the bedside, the blood collecting team adds a measured amount of blood to the distributor. Two alternative approaches can be made. The plastic dust cover can serve to prevent evaporation, or the dust cover is torn off, and the blood allowed to air dry in a rack, where it remains along with the days collection of specimens. It is to be observed that once the sample is distributed, it can be dried and stored.

Figure 5:
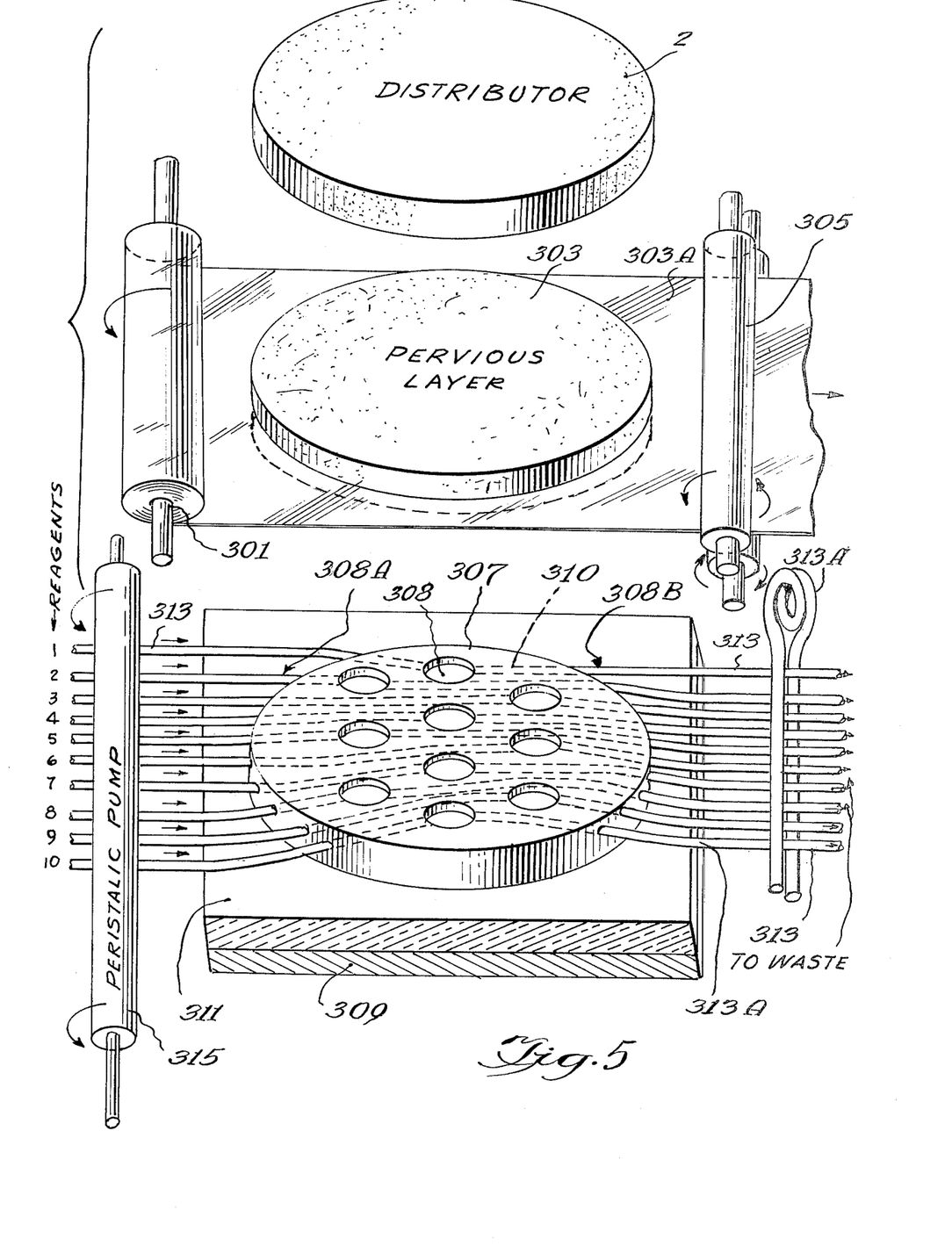
FIG. 5 shows a perspective view of yet another version of an automated system.

The samples stored on a confined distributor card can be processed in the instrument of FIG. 5. This instrument is also a multi-tape instrument and has a payoff roller 301 with reinforced porous discs 303 carried on a plastic tape 303a and a drive mechanism 305. The porous layer extends above and below the plastic disc 305. Under the porous layer 303 is a multi-pocket circular disc 307, supported on an opaque metal support 309 over which is a plastic or quartz transparent support 311. Circular disc 307 is similar to channeled disc 7 of FIG. 2h, and has a plurality or circular or cylindrical pockets. Disc 307 is about 0.1 to 1 mm thick, the pockets 308 are about 0.6 cm wide and of a depth of 0.1 to 1 mm. Each pocket 308 has an inlet 308a and an outlet 308b connected to channels 310 of about 0.1 mm in width. Resilient tubes 313 are connected to the inlet and outlet sides of each channel 310. On the inlet side of the tubes is a peristaltic pump 315, and each tube 313 is in turn connected to a reagent held in a container. The reagents may be the same or different. In the illustration given in FIG. 5, there are ten pockets 308 and ten feed tubes 313 each feeding a different reagent. In practice, the operator places the computer card into the receiving slit (not shown) of the instrument, and activates the instrument by pressing a button. This causes the reinforced porous tape disc to be pulled over the empty structure 307. Alternately, a porous disc can be placed by hand over the plastic disc containing the pockets. The distributor 21 containing the sample, now contacts the porous disc and a press plate holds the distributor, porous disc and structure containing the pockets together. At this point the reagents are pumped in from the peristaltic pump completing the system of the distributor, porous tape and film of liquid reagent, and starting the reaction. A small positive pressure is maintained in the pockets. This serves to insure close contact between the distributor, porous layer and reagent held in the pockets as they push against the press plate. This positive pressure is a result of constrictions in the exit tubes and a spring clamp which retains the solution under slight positive pressure after the air is expelled. This clamp is open when pumping reagents into the pockets and then closes just before the pump stops, thus forming a positive pressure. The opaque support 309 with small holes permits the viewing of the reagent film but blocks out the connecting channels. The structure illustrated in FIG. 5 contains cylinders of about 0.6 cm in diameter. At its widest point, that is the vertical, there are four cylinders totalling 2.4 cm or about 1 inch. Thus, for an instrument analyzing ten specimens simultaneously, a circle of about 1½ inches in diameter is needed.

Alternatively, the porous tape may be supported by an additional tape such as 1 mil filter paper which provides additional strength. This is especially useful when millipore cellulose acetate is used as the porous tape. A fine nylon weave may also support the porous layer. This may be impregnated in such a way as to form confined areas of pervious material.

The structure shown in FIG. 5 is readily constructed. Although the layer of the structure shown in FIG. 5 is shown as a circle, this is only for demonstration purposes. It is most practical to use a square piece of plastic and then drill out the holes with a ¼" drill. This is then glued to a second piece of transparent plastic or quartz sheet, and the channels are drilled with a 1/64" drill. Finally an opaque black support of metal or plastic, containing small holes for viewing the liquid medium is glued to the assembly. It will be seen that the top piece of plastic is advantageously of the same shape as the supporting layers so that the channels come to the end of the structure where they can be attached to the plastic tubing communicating to the reagents and the waste. The bottom layer, with the small holes is best made of metal. Viewed from the bottom, the observer sees an array of open circles, the opening communicating with the bottom layer supporting the liquid film medium. The cylinders of reagents are scanned by reflectance or fluorescence. After a fixed time, the distributor is removed and the change in optical properties of the solution in the cylinders is scanned.

Figure 6:
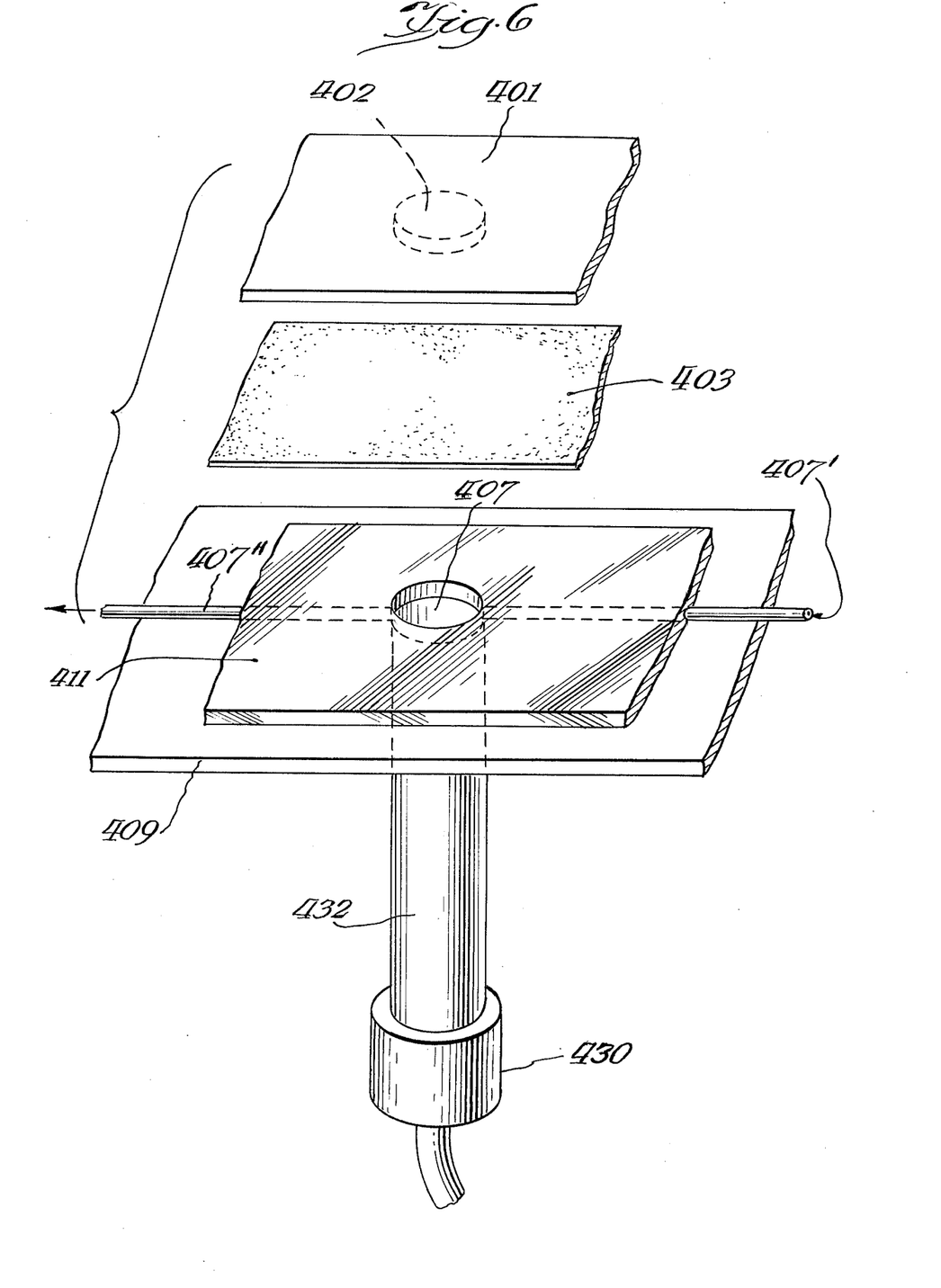
FIG. 6 is a perspective view of the use of an electrode.

The concept just described in particularly useful for use with ion specific electrodes. Shown in FIG. 6 is a multi-layer tape arrangement with a top support tape 401, a sample receiving medium 402 under the support tape 401 an intermediate porous medium 403, a bottom support layer 409, and a plastic medium 411 which has been drilled to form a liquid film medium container 407 with inlet and outlet channels 407' and 407". The parts shown in the drawing can either be a portion of an automated apparatus or can be a one-use pad of the type depicted in FIG. 2f. The liquid reagent container 407 is approximately in the center of the bottom layer of a predetermined diameter. Directly under this cylindrical container is socket 430 which carries an ion specific electrode 432. This electrode is used to assay such ions as $H^+$, $Ca^{2+}$, $Mg^{2+}$, $Na^+$, $Cl^-$, $K^+$, $NH_4^+$, $pH^+$, $pCO_2$, $PO_2$, and others. Since one cylindrical container 407 is used in the illustration given, only one reagent is used, and the channels 407' on the input side lead to the reagent on the output side, the channel 407' leads to waste.

Figures 7A, 7B, 7C:
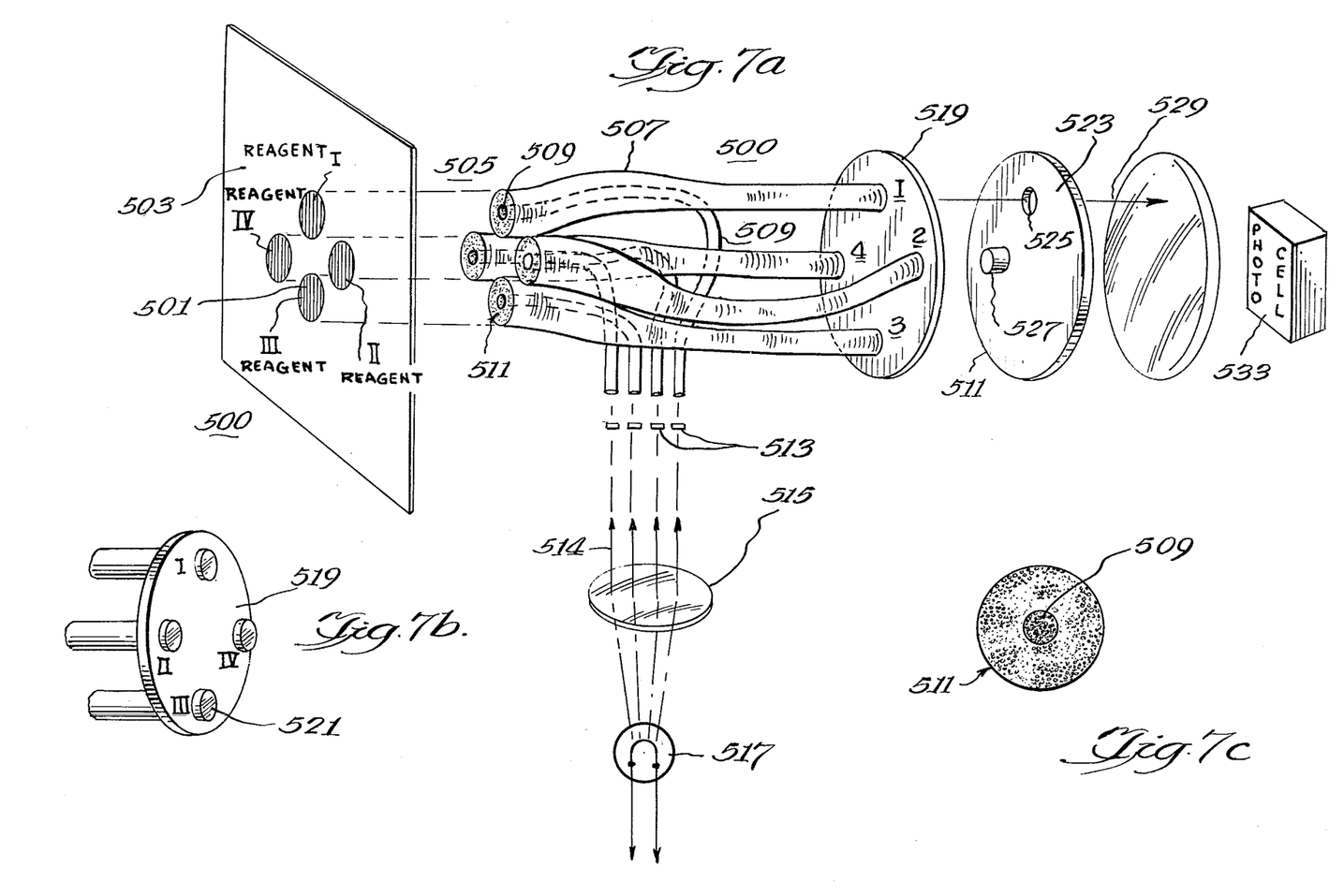
FIG. 7a shows a portion of the apparatus of FIG. 7.
FIG. 7b is another portion of the apparatus of FIG. 7.

In analyzing various samples, advantageous use can be made of fiber optics. Shown in FIG. 7a is a readout station 500 for reading out color spots 501 on a reagent film layer 503 having thereon four different reagents, I,II,III,IV. In this example, these spots are located at a predetermined position in front of the receiving ends 500 of four bundles of fiber optics 507. Each bundle 507 has two sections of fiber optics, an inner section 509 and an outer section 511. The Cassegranian principle is used. The inner section is used for illumination of the specimen being examined or assayed, while the outer section is used to collect the reflection. The reverse will also work, i.e., the outer section can be used for illumination of the specimen while the inner section can be used to collect the reflection. However, as shown in the drawing, in the present arrangement, the center or inner section is used for illumination. In each of the four bundles 507, the inner section separates from the combined bundle and leads to light filters 513 which in turn received collimated light beams 514 from a collimating lens 515 disposed over a light source 517. The outer section, 511 terminates in a stationary light station 519 and each bundle 507 has a light filter 521. Disposed in front of the stationary light station 519 is a scanner 523, or a rotating sample selector. This in turn selects only one fiber optics bundle 507 at a time, for examination through an aperture 525. Thus, the scanner 523 can turn on an axle 527 so as to place the aperture 525 before each bundle separately. Since the inner section 509 has been diverted towards the light source 517, the outer section 511 is compressed so that a compact bundle terminates in the stationary light station 519. The aperture 525 just fits over the light filter 521 and a light beam 524 from the colored spots 501 enters a focusing lens 529, entering the aperture 531 in a photocell 533. The phototube reads the sum of all the fibers from a particular spot, and irregularities in the colored spots 501 are compensated since the signal from all the fibers in each light pipe are being integrated.

For the purpose of giving those skilled in the art a better understanding of the invention, the following illustrative examples are given:

EXAMPLE I

The instrument illustrated in FIG. 5 is set up for glucose, urea, uric acid, creatinine, sodium, potassium, chloride, calcium and bilirubin determination. Four of the "pockets" are fitted with $Na^+$, $K^+$, $Ca^{2+}$, and $Cl^+$ specific ion electrodes. The other five are fitted with light pipes as shown in FIG. 7a, 7b and 7c.

The reagents used for the assay of the various components are as follows:

Glucose: The reagent solution contains albumin, 50 mg/L, adenosine triphosphate 5 mmol/L, NADP (TPN) 500 mg/L, hexokinase 10 units/ml, glucose 6-phosphate dehydrogenase 0.5 units/ml, magnesium chloride 20 mmol/L, all dissolved in 0.1 molar tris buffer pH 8.0.

Urea: The reagent solution contains urease 20 units/ml, NADH (DPNH) 250 mg/L, glutamate dehydrogenase, 25 units/ml, Ketoglutaric acid 2.5 mmol/L, all dissolved in 0.1 molar tris buffer, pH 7.6

Uric acid:, the reagent solution contains, uricase 300 units/ml, horse radish peroxidase 100 micrograms/ml, and p-hydroxy phenyl acetic acid 100 micrograms/ml, dissolved in 0.1 mol/L glycine buffer pH 9.0.

Creatine: The reagent contains creatine amidohydrolase, 2 units/ml, creatine kinase, 2 units/ml, lactate dehydrogenase 25 units/ml pyruvate kinase 25 units/ml, NADH(DPNH) 250 mg/L, and ADP 100 mg/L made up in a 0.1 molar tris buffer containing 20 mmol/L of magnesium chloride and 5 mmol/L phosphoenol pyruvate at a pH of 8.0

Bilirubin: The reagent solution contains caffein 5 mg/ml, sodium benzoate 6 mg/ml, sodium chloride 2 mg/ml, sulfanilic acid 0.5 mg/ml, sodium nitrite 5 micrograms/ml, hydrochloric acid (12 molar), 15 microliters, dissolved in water.

Sodium: The reagent solution contains 3 mmol/liter sodium chloride and 1 mmol/liter potassium chloride made up in a 0.01 molar triethanol amie solution in water adjusted to a pH of 8.2 with acetic acid.

Potassium: The reagent solution contains 0.1 mmol/liter KCl made up in a 0.01 mol/liter triethanol amine solution in water adjusted to a pH of 8.4 with acetic acid.

Chloride: The reagent solution contains 0.1 mols/liter of acetic acid in water.

Calcium: The reagent solution contains 0.1 mmol/liter of calcium nitrate in a 0.07 mol/liter solution of nitric acid.

The wavelengths used to read the glucose, urea and creatinine by fluorescence is 353 nm for excitation and 455 nm for emission. For uric acid, also read by fluorescence, excitation is at 317 nm and emission at 414 nm. Bilirubin is read by reflectance at 540 nm.

The blood sample is allowed to spread evenly on the sample distributor as shown in FIG. 1b. In the meantime, reinforced porous layer 303 of FIG. 5, covers the various pockets. The sample distributor is now placed over the porous layer, aligned over the pockets, and pressure is applied by a press plate (not shown). The components diffuse through the porous membrane (0.5 mil cellophone) to the various reagents which have been pumped into the pockets from the containers by the peristaltic pump. For glucose, urea, creatine, uric acid and bilirubin. The emitted light is brought to the stationary light station 519. Scanning wheel 523 rotates, reading the emitted monochromatic light from five sources, respectively. The data accumulated is fed to an analog to digital interface and then to the computer for analysis. The voltage changes of the ion specific electrodes are also fed to the computer by means of the interface, and interpreted in terms of concentration. The results are printed on the computer card (FIG. 1b) which is filed in the patients chart.

The pockets of the instrument of FIG. 5 are rinsed with the various reagents and a new porous disc moves into place for the assay of the next sample.

EXAMPLE II

Using the apparatus of FIG. 4, the sample distributor 216 receives the specimen from an automated feeding device such as an autodiluter, capillary dispenser, or sample pipetter. The encapsulated reagents can be those indicated in Example 1, for glucose, urea, creatinine, bilirubin and uric acid. In addition, for lactate dehydrogenase, the solution contains 0.4 mg/ml of pyruvic acid, 1 mg/ml of NADH (DPNH) made up in a phosphate buffer, 0.1 mol/L. For serum glutamate-oxaloacetate transaminase (SGOT), the solution contains 40 U/ml malate dehydrogenase, 0.3 mg/ml alpha ketoglutarate, 20 mg/ml aspartic acid, 1 mg/ml NADH, in 0.1 mol/L phosphate buffer, pH 7.4. For serum glutamate-pyruvate transaminase (SGPT), 15 mg/ml of alanine replaces the aspartic acid in the SGOT reagent above. For creatine phosphokinase, the reagent solution contains 6 mg ADP/ml, 1 mg phosphocreatine/ml, 2 mg glucose/ml, 10 units hexokinase/ml, and 1 mg NADP (TPN)/ml, made up in a pH 7.4 phosphate buffer solution 0.1 mol/l containing 1 mg albumin/ml.

The porous intermediate layer is made of cellulose acetate of a porosity to allow proteins through but not erythrocytes (e.g. 0.1 microns). This can be constructed by stretching a loose weave (e.g., 10 threads to the inch) of fine nylon thread, on a glass plate, and pouring and spreading evenly a dilute solution of cellulose acetate in a mixture of cellosolve and ethyl acetate. On evaporation, the layer appears opaque and milky. This can be made in a continuous tape using conventional equipment.

On activation, the sample is deposited on the distributor, is turned over by roller 219 and contacts the intermediate porous tape being disposed over the encapsulated reagent spots. The combined tapes move through the crusher roller 226 where the reagent is released to create a liquid film. The sample distributor, porous tape and liquid film assembly moves to the delaying zone and then to the readout zone.

While in the readout zone, the emission from the reaction products formed with the glucose, uric acid, urea, creatinine and bilirubin are scanned and evaluated by reflectance as in Example I. Similarly, the enzymes lactate dehydrogenase, SGOT, SGPT and creatine-phosphokinase are assayed by fluorescence with 353 being the excitation light and 455 being the emission being measured.

EXAMPLE III

Using the arrangements shown in FIGS. 2g and 2h, single determinations are run readily, using commercially prepared reagents, or reagents prepared in the laboratory. A few typical examples are listed here, other than those described in examples I and II. In each case the syringe is filled with the reagent and the pocket is covered with cellophane or reinforced cellulose acetate. The sample is added to the distributor which is then made to cover the porous layer and the pockets shown in FIG. 2g. The assembly is held together by a spring clip. The reagent is now forced into the pocket from the syringe, expelling the air into the overflow chamber. The color developed is read as in Example I and II. Typical reagents are as follows:

For salicylate: 1% ferric nitrate in 0.07 N $HNO_3$ read at 540 nm.

For albumin: 80micromoles/L, brom cresol green, in succinate buffer pH 4.0.

For total protein: alkaline copper solution containing 2 mg/ml copper sulfate and 125 mg/ml NaOH in water. Read at 540 nm.

For quinidine: 0.1 mol/L sulfuric acid, read by fluorescence, excitation 350 nm., emission 450 nm.

EXAMPLE IV

For radio-immunoassay estimation, the arrangement of FIG. 2g and 2h can be readily applied. The general principle is to allow a mixture of antibody and radioactive material being assayed, (e.g., morphine) to react with the serum of the patient. Some of this mixture is placed on the distributor. After incubating on the distributor of FIG. 2g, the distributor is brought into contact with the porous membrane covering the pocket. A reagent is now added to the pocket (for morphine the reagent is 0.1 mol/l acetate solution pH 6.0). Morphine not fixed to antibody diffuses to the solution in the pocket. The distributor and porous membrane are removed and the radioactive morphine which has reached the pocket is measured, as a measure of the morphine present in the serum.

What is claimed is:

1. An arrangement for the analysis of small quantities of chemical samples, comprising in combination:
   (a) a sample distributor flat first component for defining an area to receive the specimen to be analyzed;
   (b) a pervious layer second component in operational contact with said first component, said second component including positional means for positioning a section thereof of about the size of said first component;

(c) a liquid phase reagent container third component including a defined thin disc-shaped processing zone in contact with said second component having in said processing zone at least one hollow vessel, said hollow vessel having inlet and outflow channels, said inlet channel being on one side and said outflow channel being on the other side of said third component so that a liquid reagent may be introduced into said processing zone to form a thin film of a reagent, whereby the component being assayed may move through the pervious layer from the sample distributor and be evenly dispersed in the thin film of reagent for analysis.

2. An arrangement as claimed in claim 1 including pump means coupled to said inlet channel to pump a liquid phase reagent thereinto, and wash out said processing zone for reuse.

3. An arrangement as claimed in claim 1 wherein said third component has a plurality of processing zones defined therein, said first component covering said zones so as to distribute the sample to be analyzed in each zone through said pervious layer second component for the analysis of a plurality of the different contents of said sample.

4. An arrangement as claimed in claim 3 including optical photocell readout means disposed to readout the sample analyzed in each of said zones.

5. An arrangement as claimed in claim 4 wherein said readout means is a readout station whereat a sample specimen is presented for evaluation thereat on said defined thin flat processing zone, said evaluation being provided as the response of said photocell in terms of concentration of the chemical components being assayed, said arrangement including optical fiber means having an outer bundle and an inner bundle, said inner and outer bundles both having one end disposed opposite said read-out station, said bundles then separating, one of said bundles having its other end disposed to receive sample illuminating light beams from a light source, said other bundle having its other end disposed to carry a beam reflected by the sample to said photocell.

6. An apparatus as claimed in claim 5 wherein said one of said bundles is the inner bundle.

7. An apparatus as claimed in claim 5 wherein said one of said bundles is the outer bundle.

8. An arrangement for use in an apparatus for the chemical analysis of a specimen which is to be deposited in a confined area of a sample receiving first flat medium and wherein a component of said specimen is passed through a porous second medium to a reagent-containing third medium, the improvement in said arrangement wherein the third medium is a thin layer of the reagent in the liquid phase disposed in a confined area of about the same size as the confined area of the first medium.

9. An arrangement as claimed in claim 8 wherein the area of the porous medium is larger than the area of the sample receiving first medium.

10. An arrangement as claimed in claim 8 wherein said reagent comprises a first reagent means encapsulated in said confined area and at least one second reagent means capsule disposed over the first encapsulated reagent means at said defined area.

11. An arrangement as claimed in claim 10 including a spacer disposed over said third medium, said defined area having a cylindrical container defined in said spacer, and, inlet and outlet narrow channels leading to said container to feed liquid phase reagent to the container and flow out the excess reagent.

12. A liquid phase reagent analytical arrangement comprising a defined thin disc-shaped processing zone fitted with inlet and outlet channels, open at the top, in contact with a flat medium, closing the top of said disc-shaped processing zone so that a sample evenly distributed over said flat medium may be analyzed by transferring said sample evenly to a liquid reagent in said zone, said reagent being formed by said zone into a thin film.

* * * * *